United States Patent
Latere Dwan'isa et al.

(10) Patent No.: US 10,625,051 B2
(45) Date of Patent: Apr. 21, 2020

(54) INJECTION CATHETER FOR DELIVERING A THERAPEUTIC AGENT INTO A SUBSTRATE

(71) Applicant: Celyad S.A., Mont-Saint-Guibert (BE)

(72) Inventors: Jean-Pierre Latere Dwan'isa, Namur (BE); Christian Homsy, Woluwe-Saint-Pierre (BE); Jozef Bartunek, Ghent (BE); Roland Gordon-Beresford, LaHulpe (BE)

(73) Assignee: CELYAD S.A., Mont-Saint-Guibert (BE)

( * ) Notice: Subject to any disclaimer, the term of this patent is extended or adjusted under 35 U.S.C. 154(b) by 0 days.

(21) Appl. No.: 15/133,601

(22) Filed: Apr. 20, 2016

(65) Prior Publication Data

US 2016/0228677 A1 Aug. 11, 2016

Related U.S. Application Data

(63) Continuation of application No. 13/265,961, filed as application No. PCT/EP2010/055869 on Apr. 29, 2010, now Pat. No. 9,345,857.
(Continued)

(30) Foreign Application Priority Data

Apr. 29, 2009 (BE) ..................... 009/0271

(51) Int. Cl.
*A61M 25/00* (2006.01)
*A61M 5/158* (2006.01)
(Continued)

(52) U.S. Cl.
CPC .......... *A61M 25/007* (2013.01); *A61M 5/158* (2013.01); *A61M 25/0084* (2013.01);
(Continued)

(58) Field of Classification Search
CPC .......... A61M 2025/009; A61M 25/007; A61M 25/0084; A61M 2025/0087;
(Continued)

(56) References Cited

U.S. PATENT DOCUMENTS 5,334,168 A 8/1994 Hemmer
5,569,191 A 10/1996 Meyer
(Continued)

FOREIGN PATENT DOCUMENTS

EP 0810003 12/1997
EP 1 381 418 B1 11/2006
(Continued)

*Primary Examiner* — Emily L Schmidt
(74) *Attorney, Agent, or Firm* — Nixon Peabody LLP

(57) ABSTRACT

The invention relates to an injection catheter for delivering a therapeutic agent into a substrate, comprising one or more lumens and a curved delivery element, said lumen serving as a guide for said curved delivery element outside of the substrate; said curved delivery element comprising openings on its distal tip, said distal tip comprising a distal zone and a proximal zone, said injection catheter being characterized in that the specific surface in said distal zone of said distal tip of said curved delivery element is higher than the specific surface in said proximal zone of said distal tip of said curved delivery element. The invention also relates to a process for delivering a therapeutic agent into a substrate.

22 Claims, 5 Drawing Sheets

Related U.S. Application Data

(60) Provisional application No. 61/312,371, filed on Mar. 10, 2010.

(51) Int. Cl.
*A61B 17/00* (2006.01)
*A61B 18/00* (2006.01)

(52) U.S. Cl.
CPC ............... *A61B 2017/00247* (2013.01); *A61B 2018/00392* (2013.01); *A61M 2005/1581* (2013.01); *A61M 2025/009* (2013.01)

(58) Field of Classification Search
CPC .. A61M 2025/0089; A61M 2025/0085; A61M 2025/0092
See application file for complete search history.

(56) References Cited

U.S. PATENT DOCUMENTS

| | | | |
|---|---|---|---|
| 5,569,197 A | 10/1996 | Helmus | |
| 6,302,870 B1 * | 10/2001 | Jacobsen | A61B 17/22 604/164.09 |
| 6,595,958 B1 * | 7/2003 | Mickley | A61M 25/0041 604/164.01 |
| 6,626,885 B2 | 9/2003 | Massengale | |
| 7,094,230 B2 | 8/2006 | Flaherty | |
| 2002/0052576 A1 | 5/2002 | Massengale | |
| 2002/0082547 A1 | 6/2002 | Deniega | |
| 2004/0002677 A1 | 1/2004 | Gentsler | |
| 2005/0165354 A1 * | 7/2005 | Schwartz | A61M 5/158 604/152 |
| 2005/0234390 A1 | 10/2005 | Buckman | |
| 2007/0005018 A1 * | 1/2007 | Tekbuchava | A61M 25/003 604/164.01 |
| 2007/0021730 A1 | 1/2007 | Flaherty | |
| 2007/0048726 A1 | 3/2007 | Baust | |
| 2007/0140914 A1 * | 6/2007 | Sawa | A61M 25/1002 422/400 |
| 2007/0255230 A1 * | 11/2007 | Gross | A61B 17/8811 604/272 |
| 2008/0045996 A1 | 2/2008 | Makower | |
| 2008/0276643 A1 | 11/2008 | Heroux | |
| 2009/0204079 A1 * | 8/2009 | Nimkar | A61M 25/001 604/246 |

FOREIGN PATENT DOCUMENTS

| | | |
|---|---|---|
| WO | WO 01/05210 | 1/2001 |
| WO | WO 02/056937 | 7/2002 |
| WO | WO 02/083228 | 10/2002 |
| WO | WO 2005/049110 | 6/2005 |
| WO | WO 2009/049823 | 4/2009 |
| WO | WO 2010/125166 | 11/2010 |

\* cited by examiner

INJECTION CATHETER FOR DELIVERING A THERAPEUTIC AGENT INTO A SUBSTRATE

CROSS-REFERENCE TO RELATED APPLICATIONS

This application is a continuation of U.S. application Ser. No. 13/265,961, filed Dec. 13, 2011, which is a 35 U.S.C. § 371 National Phase Entry Application of International Application No. PCT/EP2010/055869 filed Apr. 29, 2010, which designates the U.S., and which claims benefit of Belgium Application No. BE2009/0271 filed Apr. 29, 2009 and claims benefit under 35 U.S.C. § 119(e) of U.S. Provisional Application No. 61/312,371 filed Mar. 10, 2010, each of which is hereby incorporated by reference herein in its entirety.

TECHNICAL FIELD

The invention relates to the field of injection catheters. More specifically, the invention relates to an injection catheter for delivering a therapeutic agent into a substrate and a process for injecting a therapeutic agent into a substrate.

DESCRIPTION OF THE STATE OF THE ART

Cardiovascular diseases are among the principal causes of death in the world. Heart attacks and myocardial infarction may cause immediate death or a relatively high morbidity rate, considering the irreversible damage caused to the heart. The prevention and treatment of these diseases are thus a major issue and numerous clinical efforts are being made to improve the care and treatment of cardiac disorders.

Regenerative medicine is one of the current research methods for reducing dysfunction of organs, such as the heart, for example (Sherman, *Cellular Therapy for Chronic Myocardial Disease: Nonsurgical approaches, Basic Appl. Myol.* 13(1) 11-14). This involves the injection of therapeutic solutions directly into the organ through devices. Such therapy is promising but requires some optimizations. One of the limitations is the low rate of retention of the therapeutic solutions injected into the organ, due to its porosity. In the case of the heart muscle, this rate of retention varies but does not exceed 5 to 10% depending on the injection methods used (Bartunek et al., *Delivery of Biologics in Cardiovascular Regenerative Medicine, Clinical Pharmacology & Therapeutics,* 2009). This low rate of retention thus implies a non-optimal efficiency of these therapeutic solutions. In addition, during the comparative tests conducted by inventors, a device of the prior art, the Myostar® device developed by Biosense-Webster, was evaluated and showed a retention of around 25,000 microspheres per gram (see FIG. 8 and its description). This level of retention is not optimal for therapeutic agent delivery and can be markedly improved.

Therapeutic solutions are generally administered with the help of medical devices such as injection catheters, for example, whose configuration directly affects the efficiency and the quality of the injection. Heldman et al., Cell Therapy for myocardial infarction: Special delivery, *Journal of Molecular and Cellular Cardiology,* 2008, 44, 473-476, describes the disadvantages of several delivery devices listed according to type of injection (epicardiac, endocardiac, intracoronary or intravenous). Within the framework of an endocardiac injection, the risk of perforation of the heart muscle is accentuated because such a complication may lead to the patient's death.

EP 1 301 228 discloses a deployment device intended for the heart. The device is an injection catheter whose tip in contact with the heart muscle is fitted with a hole on one of its faces. Cellular material may then be ejected into the heart muscle through said hole. However, the cellular material is injected at a precise isolated point in the heart muscle that does not aid in its dissemination. Furthermore, when the tip is withdrawn, some of the cellular material may be released in the ventricle. In addition to a low rate of retention in the heart tissue and a risk of perforation of the heart muscle, the injection at an isolated point may promote the formation of edema.

US 2007/005018 discloses a direct injection catheter device comprised of a hollow insertion tube (410) fitted with curved elements (310) equipped with regular openings (734) at their tip. Said elements are used to anchor the insertion tube in the heart muscle and partially reduce the risk of perforation through it. The regular openings placed on said elements serve to inject the therapeutic solution at a low speed. However, the proposed device does not allow the injection pressure and the dissemination of the therapeutic solution within the heart muscle to be controlled.

WO 01/45548 discloses a straight injection needle comprising a porous distal portion creating a gradient of hydraulic impedance on liquid moving through the pores of the distal portion. The injection needle can be connected to a surgical instrument. To achieve the delivery of the liquid with the hydraulic impedance, the porous distal portion has, in any event, porosity in the range from 50% to 85%. However, a needle having porosity higher than 20% may lack rigidity to provide a satisfactory deployment within a substrate, such as a biological tissue. Moreover, the injection needle is not provided with means to avoid the perforation of the substrate or for anchoring it into the substrate during the delivery. Hence, the delivery of a liquid cannot be properly performed with such injection needle, particularly in a beating heart muscle. In addition, the rate of injection is in the range from 0.1 cc per second to 2 cc per second. Such injection rate is not suitable for injecting therapeutic agent comprising cells since the membrane of the cells will be damaged.

There is thus a need for an injection catheter capable of delivering a therapeutic agent into a substrate as said therapeutic agent is disseminated in said substrate, while still minimizing the losses of said therapeutic agent when the catheter needle is withdrawn and the risk of perforation of said substrate, while at the same time maximizing the retention of said therapeutic agent in said substrate. There is also a need for an injection catheter capable of delivering a therapeutic agent into a substrate while still limiting the risk of edema at the injection site.

SUMMARY OF THE INVENTION

The present invention overcomes all or some of the drawbacks and disadvantages of conventional techniques and may also offer other advantages not envisaged with conventional devices.

According to a first aspect of the invention, an injection catheter for delivering a therapeutic agent into a substrate is provided. Said injection catheter consists of one or more lumens and a curved delivery element, said one or more lumens serving as guide for said delivery element outside of the substrate, said delivery element comprising openings at its distal tip, said distal tip consisting of a distal zone and a proximal zone; said injection catheter is characterized in that the specific surface of said openings of said distal zone is higher than the specific surface of said openings of said proximal zone. A specific surface increasing between said proximal zone and said distal zone allows for better retention of the therapeutic agent in the substrate due to the optimal distribution of said therapeutic agent in said substrate.

According to a second aspect of the invention, a process for delivering a therapeutic agent into a substrate through an injection catheter according to the invention is provided. Said process comprises the steps of:
- positioning the distal tip of said injection catheter on the surface of the substrate,
- sliding said curved delivery element inside said one or more lumens and extending it inside the substrate,
- injecting the therapeutic agent into the substrate through said curved delivery element.

According to another aspect, the invention relates to the use of the injection catheter, according to the invention, for delivering a therapeutic agent into a substrate.

DETAILED DESCRIPTION OF THE INVENTION

The term "catheter", as used here, refers to a tubular medical device for insertion into a duct, a body cavity, veins or arteries in order to allow for the injection or withdrawal of fluids or to keep a pathway open.

The term "lumen" refers to the opening or the inside space of a hollow tubular element facilitating the insertion of a second element or the injection of a liquid in a duct, a body cavity, veins or arteries.

The term "delivery element" as used here refers to a tube with a distal opening; a proximal opening on which a cap also called "luer lock" may be adapted. This cap serves to close the proximal opening of the delivery element in a secured manner.

The term "specific surface" refers to the sum of the surfaces of the openings present in a predefined zone of the distal tip of a delivery element, in relation to the delivery element's unit of length. Hereinafter, the specific surfaces are expressed in $mm^2$ of opening per mm of length of delivery element.

Figure 1A:
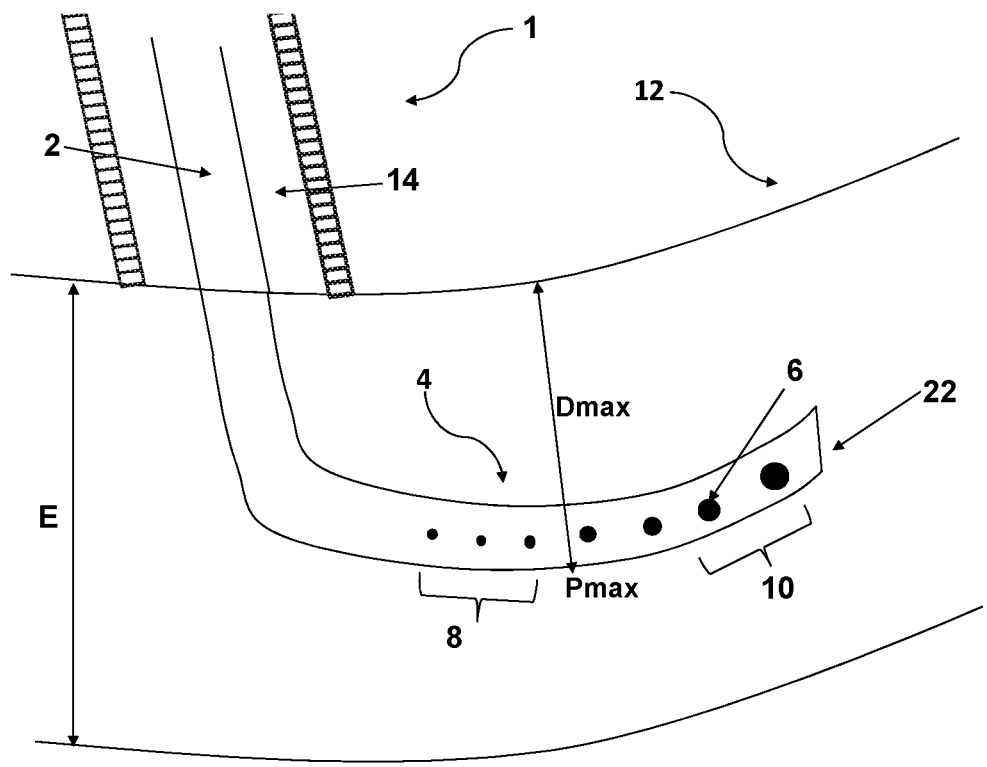
FIG. 1A represents a schematic view of an injection catheter according to a particular embodiment of the present invention.

The substrate has a thickness E. Referring to FIG. 1A, the curved delivery element 2 penetrates the substrate 12 to a depth that varies according to the point P of the delivery element being considered. The shortest possible distance between the point P being considered and the surface of the substrate is the depth D. The maximum depth Dmax is located at the point Pmax for which the distance D is the greatest. The term "penetration depth" refers to the relation, expressed as a percentage, between the maximum depth Dmax and the thickness of the substrate E.

FIG. 1A represents a schematic view of the distal tip 4 of the curved delivery element 2. The injection catheter 1 is positioned on the substrate 12 and comprises a lumen 14 in which a delivery element 2 is deployed. The distal tip 4 of the delivery element 2 comprises openings 6 on at least one side. The delivery element is curved. The distal tip 4 comprises a proximal zone 8 and a distal zone 10. Said distal zone 10 is comprised of at least one opening 6. Said distal zone 10 may be located anywhere along the distal tip 4 on the condition that it is closer to the distal opening 22 than said proximal zone 8. The distal opening 22 is not considered to be an opening 6 according to the present invention. Said distal zone 10 and said proximal zone 8 have identical dimensions. The length of the distal tip 4 corresponds to the distance between the opening closest to the distal opening 22 and the opening farthest from said distal opening 22. The distal tip may not exceed three centimeters.

Figure 1B:
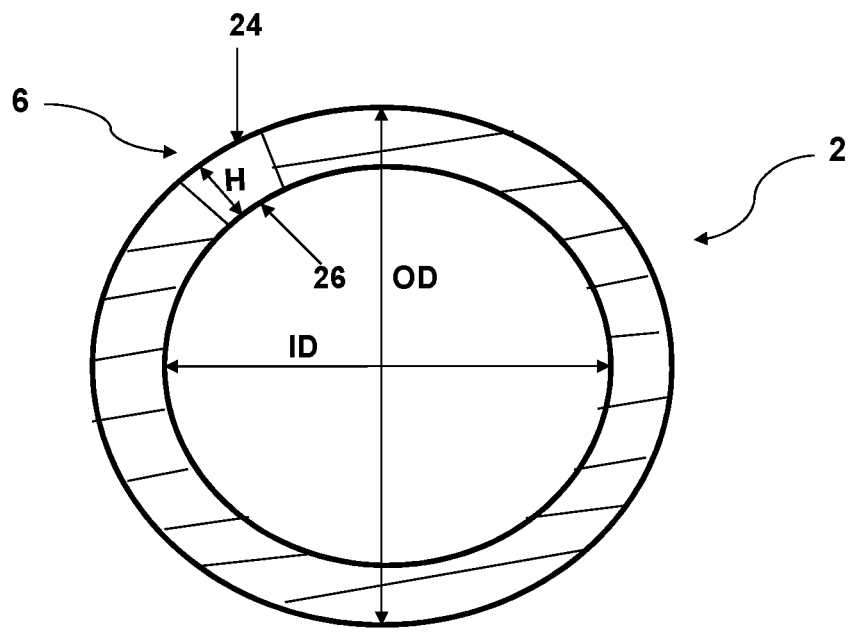
FIG. 1B represents a cross-section of a delivery element according to a particular embodiment of the present invention.

FIG. 1B represents a cross-section of the curved delivery element 2 at the level of the distal tip 4. Said curved delivery element has an inner diameter ID and an outer diameter OD. Said delivery element is comprised of an opening 6. The opening 6 has a three-dimensional shape with an outer surface 24 and an inner surface 26, and extends to a height H. The term "surface" used in the present invention refers to the outer surface 24 of the opening 6. The opening may have an inner surface 26 that is equal to, larger than or smaller than the outer surface 24. The shape of the opening as described in the invention is the shape at the level of the outer surface 24 of said delivery element 2.

According to a first aspect, the present invention relates to an injection catheter 1 for delivering a therapeutic agent into a substrate comprising one or more lumens 14 and a curved delivery element 2, said one or more lumens serving as guide for said curved delivery element 2 outside of the substrate 12, said curved delivery element 2 comprising openings 6 at its distal tip 4, said distal tip 4 comprising a distal zone 10 and a proximal zone 8, said injection catheter 1 being characterized in that the specific surface of said openings 6 in said distal zone 10 of the distal tip 4 of said curved delivery element 2 is higher than the specific surface of said openings 6 in said proximal zone 8 of the distal tip 4 of said curved delivery element 2. A specific surface of said openings 6, increasing between said proximal zone 8 and said distal zone 10, makes it possible to establish a controlled distribution of the therapeutic agent inside the substrate, which will result in better retention of said therapeutic agent in the substrate. Said curved delivery element comprises a plurality of openings at its distal tip. The number of openings may vary between 2 and 100, preferably between 2 and 50 and more preferably between 2 and 20. The number of openings can be 2, 3, 4, 5, 6, 7, 8, 9, 10, 11, 12, 13, 14, 15, 16, 17, 18, 19 or 20, or a value comprises in the range set by two of any of the above-mentioned values. Preferably, the injection catheter may comprise one lumen. When the delivery element 2 is contained in the catheter lumen 14, the delivery element is maintained under a substantially straight straight form. When deployed into the substrate, the delivery element 2 takes its curved shape.

In an embodiment, the specific surface of said openings 6 in said distal zone 10 and in said proximal zone 8 of said distal tip 4 may be between 0.01 mm$^2$/mm and 0.25 mm$^2$/mm, and more preferably between 0.015 mm2/mm and 0.1 mm$^2$/mm.

In a preferred embodiment, the specific surface increases between said proximal zone 8 and said distal zone 10 through the increase in the mean surface of the openings 6 between said proximal zone 8 and said distal zone 10 of the distal tip 4 of said curved delivery element 2. The term "mean surface" refers to the sum of the surfaces of said openings 6 in a zone is under consideration divided by the number of said openings 6 in the zone under consideration, that is, the proximal zone 8 or the distal zone 10 of said distal tip 4 of the curved delivery curved element 2. Preferably, the mean surface of said openings 6 may be between 0.001 mm$^2$ and 0.06 mm$^2$. More preferably, the mean surface of said openings 6 may be between 0.007 mm$^2$ and 0.02 mm$^2$.

In another preferred embodiment, the specific surface increases between said proximal zone 8 and said distal zone 10, through the increase in the density of said openings 6 between said proximal zone 8 and said distal zone 10. The term "density" refers to the number of openings per mm$^2$ of surface of the curved delivery element 2 in a predefined zone, that is, the proximal zone 8 or the distal zone 10. Thus, the density of said openings 6 in said distal zone 10 and in said proximal zone 8 may be between 0.04 openings/mm$^2$ and 25 openings/mm$^2$.

In another preferred embodiment, the specific surface increases between said proximal zone 8 and said distal zone 10 through the increase in the density and the mean surface of said openings 6 in said proximal zones 8 and distal zones 10.

In another preferred embodiment, the specific surface increases between said proximal zone 8 and said distal zone 10 through the increase in the total surface of the openings 6. The total surface of the openings refers to the sum of the surfaces of each opening 6 in said zone under consideration, such as said distal zone 10 and said proximal zone 8, for example. The total surface of the openings in a zone, such as the proximal zone 8 and the distal zone 10, for example, may be between 0.001 mm$^2$ and 1.5 mm$^2$. In said distal 10 and proximal zones 8, the surface of the openings may be regular, increasing or decreasing in a distal direction over all or part of said zones on the condition that the specific surface of said openings in said distal zone 10 is higher than that of said openings in said proximal zone 8.

In a preferred embodiment, said openings 6 may have various shapes such as oval, square, circular, rectangular, triangular, ellipsoid or they may also be slit-shaped, rhomboidal, spiral or helical. Said openings 6 may be located anywhere along all of the faces of the distal tip 4 of said curved delivery element 2. In addition, said openings may allow cells with a diameter of 10 to 1560 μm to pass through.

In another preferred embodiment, the injection catheter 1 also includes a means of controlling the penetration depth of said delivery element into the substrate. The presence of said means of control has made it possible to avoid and circumvent the problems related to the risk of perforation of the substrate. Thus, said means of control make it possible, in a controlled manner, to maintain the penetration depth at between 25% and 75% of the thickness of said substrate. The therapeutic agent may thereby be injected into the substrate in complete safety.

In particular, said means to control the penetration depth may be a curved element with shape memory, an element equipped with a stop or an element detectable by ultrasound or radiodetectable techniques such as fluoroscopy, for example. Taking its configuration into account, the injection catheter, according to the invention, may penetrate the substrate to a significant distance, de facto increasing the surface of the substrate treated with the therapeutic agent. The increase in the surface of the substrate in contact with the therapeutic agent has made it possible to increase its availability in the substrate and thereby affects the overall retention of said therapeutic agent in the substrate.

Preferably, said means of controlling the penetration depth may be a curved element with shape memory. In particular, said curved element with shape memory may be said curved delivery element 2 comprised of openings 6 at its distal tip 4, said distal tip 4 comprised of a distal zone 10 and a proximal zone 8, said curved delivery element 2 being characterized in that the specific surface of said openings 6 of said distal zone 10 is higher than the specific surface of said openings 6 of said proximal zone 8. Thus, the penetration depth of said curved delivery element 2 in the substrate is controlled by its curvature. The curvature of said curved delivery element 2 is defined by the angle between the longitudinal axis going through the center of said lumen when the injection catheter is positioned on the substrate and the longitudinal axis going through the center of the distal opening 22 after deployment of said curved delivery element 2 in the substrate. Preferably, the angle may be between 60° and 120°, more preferably between 80° and 120°. In particular, the angle may be between 85° and 100°. Preferably, the curvature of the distal tip 4 may be constant.

Alternatively, said means of controlling the penetration depth may be an element equipped with a stop, not shown in the figures. In particular, said element equipped with a stop may be said curved delivery element 2. Thus, said curved delivery element 2 may be equipped with a stop placed at its proximal tip to determine its penetration depth in the substrate.

Alternatively, said means of controlling the penetration depth may be an element detectable by ultrasound or radiodetectable techniques such as fluoroscopy, for example. In particular, said detectable element may be said curved delivery element 2 comprised of openings 6 at its distal tip 4, said distal tip 4 comprised of a distal zone 10 and a proximal zone 8, said curved delivery element 2 being characterized in that the specific surface of said openings 6 of said distal zone 10 is higher than the specific surface of said openings 6 of said proximal zone 8.

According to a preferred embodiment, said injection catheter may comprise anchoring means to avoid the removal of the curved delivery element during the delivery of the therapeutic agent. Said anchoring means can be the curved delivery element.

The delivery element can be retractable. The delivery element can retract when force is not exerted on the push button, disposed around the luer lock, due to an opposite force being exerted by a spring located distally of the luer lock.

According to a preferred embodiment, said curved delivery element 2 may be a hollow needle or a sleeve positioned around a piercing element. Said curved delivery element may have an outer diameter between 20 gauge and 34 gauge, preferably between 25 gauge and 32 gauge. Thus, the outer diameter of said delivery element may be 0.184 mm and 0.908 mm. Preferably, the outer diameter of said delivery element may be between 0.235 mm and 0.514 mm. Generally, the inner diameter of said delivery element may be between 0.0826 mm and 0.603 mm; preferably the inner diameter may be between 0.108 mm and 0.260 mm. The length of the delivery element may be greater than 100 cm from its distal opening 22 to its proximal tip. For example, the length of the delivery element may be approximately 120 cm. The inner and outer diameter of the section of the delivery element which penetrates the substrate may be uniform.

According to a preferred embodiment, the total surface of the openings 6 on the distal tip 4 of said curved delivery element 2 may be between 0.002 mm$^2$ and 3.0 mm$^2$. The term "total surface of the openings 6 on the distal tip 4" refers to the sum of the surfaces of each opening comprised on the distal tip of the delivery element. More preferably, the total surface of the openings 6 of the distal tip 4 may be between 0.2 mm$^2$ and 3.0 mm$^2$, most preferably between 0.3 mm$^2$ and 2.0 mm$^2$. Alternatively, the total surface of the openings 6 of the distal tip 4 may be between 0.02 mm$^2$ and 3.0 mm$^2$. Thanks to these mean surface values of said openings, the therapeutic agent is distributed regularly within the substrate, allowing for better assimilation of said therapeutic agent in the substrate and thereby avoiding the formation of edema at the level of the injection site.

According to a preferred embodiment, the curved delivery element 2 may be a hollow needle. Said hollow needle may comprise a sharp point to penetrate the substrate 12. Said hollow needle may be a material with shape memory. The term "material with shape memory" refers to a material having the capacity to remember its initial shape and to return to it even after deformation. The material with shape memory may be a nickel and titanium alloy, a copper-based, a cobalt-based, a chromium-based or an iron-based alloy. Preferably, the material with shape memory may be a nickel and titanium alloy such as NiTINOL, for example. The nickel and titanium alloy may also contain a small quantity of copper, iron, niobium, palladium or platinum. According to a preferred embodiment, the distal tip of said hollow needle is comprised of said openings. Preferably, the distal tip of said hollow needle has an open surface of between 0.5% and 30%; more preferably, the distal tip of said hollow needle has an open surface of between 2% and 20%. The term "open surface" corresponds to the percentage of the total surface of said openings compared to the total surface of the distal tip of said delivery element. Such an open surface allows for optimal use of the injection catheter, according to the invention. Said hollow needle remains sufficiently rigid to be able to penetrate the substrate while maximizing the introduction of the therapeutic agent into it. Beyond 20%, said needle loses rigidity and prevents its satisfactory deployment within the substrate. Below 2%, the small specific surface of the openings does not allow for controlled distribution of the therapeutic agent and reduces its retention to a minimum within the substrate.

According to another preferred embodiment, the delivery element may be a sleeve positioned around a piercing element. Said piercing element serves to perforate the substrate and to guide the sleeve inside the substrate. Said piercing element may be a material with shape memory as defined above. In this configuration, said openings are positioned on the distal tip of said sleeve. The distal tip of said sleeve is thus equal to said distal tip 4 of said curved delivery element 2 as defined above. Said sleeve may be made of a polymer material, a composite material, a metal or an alloy. For example, said sleeve may be of, but not limited to, polyimide, polyetheretherketone or stainless steel. Preferably, said sleeve may have an open surface higher than 2%. More preferably, said sleeve may have an open surface of between 2% and 50%. Said sleeve may thus have an open surface higher than 20%. In effect, thanks to its configuration, when the delivery element is a sleeve positioned on a piercing element, the disadvantages associated with the lack of rigidity of a delivery element having an open surface higher than 20% are avoided.

The injection catheter may be equipped with a pump controlling the injection pressure of the therapeutic agent. The presence of said pump makes it possible to maintain a constant pressure at the proximal tip of the injection catheter. Constant pressure during the injection and controlled distribution of the therapeutic agent through said openings present at the distal tip of the delivery element make it possible to minimize, limit and even avoid the risk of edema located at the level of the points of injection. In addition, the injection flow rate of the therapeutic agent through the catheter may not be too high. Thus, according to a preferred embodiment, the injection flow rate may be less than 6 ml per minute; preferably, the injection flow rate may be less than 3 ml per minute.

According to another preferred embodiment, the specific surface is of the openings may increase in a linear manner. Preferably, the distribution of the openings on said distal tip may be homogenous. The term "homogenous" refers to identical spacing between two openings. The spacing between two openings is calculated between the centers of said two openings.

According to a second aspect, the present invention relates to a process for delivering an agent into a substrate through an injection catheter according to the invention, characterized in that it comprises the following steps:
positioning the distal tip 4 of said injection catheter 1 on the surface of the substrate 12,
sliding said curved delivery element 2 of said injection catheter 1 inside the lumen 14 and deploying it inside the substrate 12,
injecting the therapeutic agent into the substrate 12 through said curved delivery element 2.

According to a preferred embodiment, the injection catheter may be equipped with a pump controlling the pressure of the injection of the therapeutic agent. The presence of said pump makes it possible to maintain constant pressure at the distal tip of the curved delivery element. According to a preferred embodiment, the pressure exerted by the pump on the proximal tip of the catheter to deliver the therapeutic agent is substantially constant for the duration of the curved delivery of said therapeutic agent. Constant pressure of the injection and controlled distribution of the therapeutic agent makes it possible to minimize, limit and even avoid the risk of edema located at the level of the injection points. In addition, the injection flow rate of the therapeutic agent through the catheter may not be too high. Thus, according to a preferred embodiment, the injection flow rate may be less than 6 ml per minute; preferably, the injection flow rate may be less than 3 ml per minute. The injection flow rate may be constant.

According to another preferred embodiment, the therapeutic agent is delivered over a period of between 20 seconds and 3 minutes for a 1 ml quantity of agent.

According to another preferred embodiment, the process of the present invention may also include a step to control the penetration depth of is said delivery element 2 into said substrate 12. Preferably, said penetration depth may be between 25% and 75% of the thickness of the substrate 12. Controlling the depth of penetration into the substrate makes it possible to avoid and to circumvent the problems associated with the risk of perforation of the substrate. The therapeutic agent may thereby be injected into the substrate in complete safety.

According to another preferred embodiment, said delivery element used in the delivery process, according to the invention, comprises openings on its distal tip. Said distal tip includes a distal zone and a proximal zone, said delivery element is characterized in that the specific surface in said distal zone of said distal tip being higher than the specific surface in said proximal zone of said distal tip. A specific surface of said openings, increasing between said proximal zone and said distal zone, makes it possible to impose a controlled distribution of the therapeutic agent inside the substrate, which will result in better retention of said therapeutic agent in the substrate. According to a preferred embodiment, the specific surface in said distal zone 10 and in said proximal zone 8 of the distal tip may be between 0.01 mm$^2$/mm and 0.25 mm$^2$/mm.

According to a preferred embodiment, the mean surface of an opening may increase between said proximal zone and said distal zone of the distal tip of said delivery element. Preferably, the mean surface of said opening may be between 0.001 mm$^2$ and 0.06 mm$^2$. More preferably, the mean surface of said openings may be between 0.007 mm$^2$ and 0.02 mm$^2$. According to another preferred embodiment, the density of said openings may increase between said proximal zone and said distal zone. Thus, the density of said openings in said distal zone and in said proximal zone may be between 0.04 openings/mm$^2$ and 25 openings/mm$^2$.

According to a preferred embodiment, the total surface of the openings on the distal tip of said delivery element may be between 0.002 mm$^2$ and 3.0 mm$^2$. The term "total surface" refers to the sum of the surfaces of each opening comprised on the distal tip of the delivery element. More preferably, the total surface of the openings of the distal tip may be between 0.2 mm$^2$ and 3.0 mm$^2$, most preferably between 0.3 mm$^2$ and 2.0 mm$^2$. Alternatively, the total surface of the openings 6 of the distal tip 4 may be between 0.02 mm$^2$ and 3.0 mm$^2$. The increase in the surface of the substrate in contact with the therapeutic agent has made it possible to improve its availability in the substrate and thereby affect the total retention of said therapeutic agent in the substrate.

According to another preferred embodiment, said openings 6 may have various shapes such as oval, square, rectangular, triangular, ellipsoid, or they may also be slit-shaped, rhomboidal or spiral. Said openings may be located anywhere on all of the faces of the distal tip of said delivery element.

The penetration depth of said delivery element into said substrate may be controlled by a curved element with shape memory, an element equipped with a stop or an element detectable by ultrasound or other radiodetectable technique such as fluoroscopy, for example.

Preferably, the penetration depth may be controlled by a curved element with shape memory. In particular, said curved element with shape memory may be said delivery element comprised of openings on at least one of the faces of its distal tip, characterized in that the openings having a specific surface increasing in the distal direction on at least a portion of said distal tip of said needle. Thus, the penetration depth of said delivery element in the substrate is controlled by its own curvature. The curvature of said curved delivery element 2 is defined by the angle between the longitudinal axis running through the center of said lumen when the injection catheter is positioned on the substrate and the longitudinal axis running through the center of the distal opening 22 after the deployment of said curved delivery element 2 in the substrate. Preferably, the angle may be between 60° and 120°; more preferably, between 80° and 120°. In particular, the angle may be between 85° and 100°. Preferably, the curvature of the distal tip 4 may be constant.

Alternatively, the penetration depth may be controlled by an element equipped with a stop. In particular, said element equipped with a stop may be said delivery element comprised of openings on at least one of the faces of its distal tip, characterized in that the openings having a specific surface increasing in the distal direction on at least a section of said distal tip of said delivery element. Thus, said delivery element is equipped with a stop placed at its proximal tip to determine the depth of its penetration in the substrate.

Alternatively, the penetration depth may be controlled by an element detectable by ultrasound or radiodetectable techniques (for example X-ray, fluoroscopy or magnetic resonance imaging). In particular, said detectable element may be said delivery element comprised of openings on at least one of the faces of its distal tip, characterized in that the openings having a specific surface increasing in the distal direction on at least a section of said distal tip of said delivery element.

According to a preferred embodiment, said delivery element used in the process, according to the invention, may be a needle or a sleeve positioned around a piercing element. If the delivery element is a needle, said needle may have an open surface of between 0.5% and 30%, preferably between 2 and 20%. In addition, said needle may be a material with shape memory as defined above. Alternatively, the delivery element may be a sleeve positioned around a piercing element. Said piercing element serves to perforate the substrate and to guide the sleeve inside the substrate. Said piercing element may be a material with shape memory as defined above. Said sleeve may be made of a polymer material, a composite material, a metal or an alloy. For example, said sleeve may be of, but not limited to, polyimide, polyetheretherketone or stainless steel. Preferably, said sleeve may have an open surface higher than 2%. More preferably, said sleeve may have an open surface of between 2% and 50%. Said sleeve may thus have an open surface higher than 20%. In fact, thanks to its configuration, when the delivery element is a sleeve positioned on a piercing element, the disadvantages associated with the lack of rigidity of a delivery element with an open surface higher than 20% are circumvented. If the delivery element is a sleeve positioned around a piercing element, the process, according to the invention, may also include a step to withdraw said piercing element prior to the injection of said therapeutic agent into the substrate.

In a third aspect, the present invention concerns the use of an injection catheter, according to the invention, for delivering a therapeutic agent into a substrate. In a preferred embodiment, the substrate may be an organ. Preferably, the substrate may be the myocardium, the liver, the kidney, the pancreas, the spinal cord or the brain. More preferably, the substrate may be the myocardium. In a preferred embodiment, the therapeutic agent may be a solution comprised of an element having a therapeutic effect on said substrate. For example, the therapeutic agent may be, but not limited to, a solution containing cells or macromolecules such as proteins, for example, growth hormones, drugs, natural or synthetic micro- or nano-particles. For example, the cells used as a therapeutic agent may have a diameter of 10 to 60 μm. Alternatively, the therapeutic agent may be any agent known in the art. Preferably, the therapeutic agent is a solution containing cells or stem cells.

EXAMPLES

The terms and descriptions used here are proposed only for illustration purposes and do not constitute limitations. Man skilled in the art will recognize that numerous variations are possible in the spirit and the scope of the invention as described in the following claims and their equivalents; in them, all terms must be understood in their broadest sense unless otherwise indicated.

Figure 2:
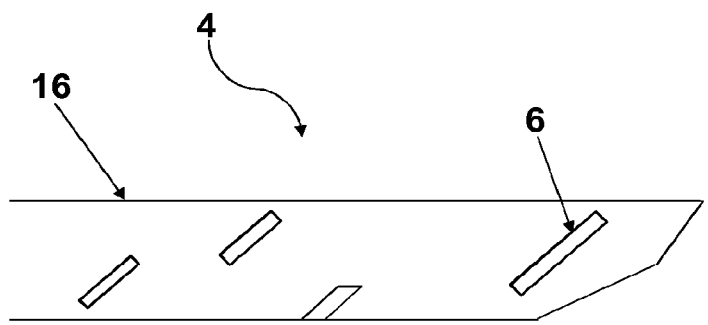
FIG. 2 represents a view of a delivery element comprising slits with a surface increasing in the distal direction.

FIG. 2 represents a schematic view of the distal tip 4 of the curved delivery element 2 comprising openings 6 with surface increasing in the distal direction according to an embodiment of the invention. The curved delivery element 2 is a hollow needle 16. The openings are in the shape of slits with surface increasing in the distal direction.

Figure 3:
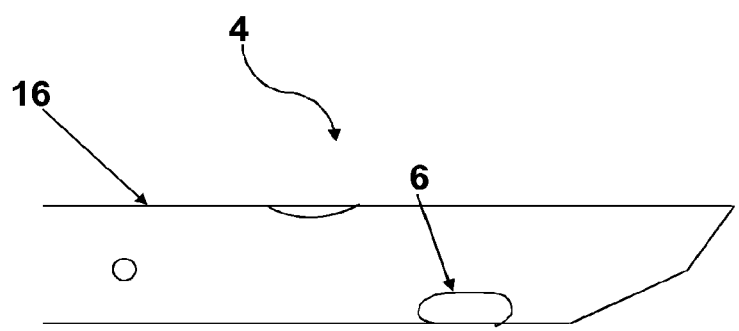
FIG. 3 represents a view of a delivery element comprising circular openings with a diameter increasing in the distal direction.

FIG. 3 represents a schematic view of the distal tip 4 of the curved delivery element 2 comprising circular openings 6 with diameter increasing in the distal direction according to an embodiment of the invention. The curved delivery element is a hollow needle 16.

Figure 4:
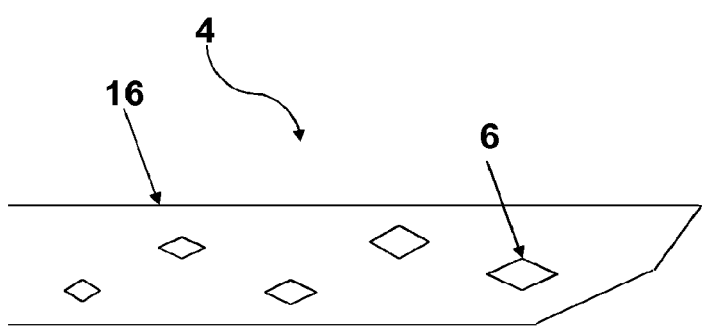
FIG. 4 represents a view of a delivery element comprising rhomboidal openings with a surface increasing in the distal direction.

FIG. 4 represents a schematic view of the distal tip 4 of the curved delivery element 2 comprising rhomboidal openings 6 with surface increasing in distal direction, according to an embodiment of the invention. The curved delivery element 2 is a hollow needle 16.

Figure 5:
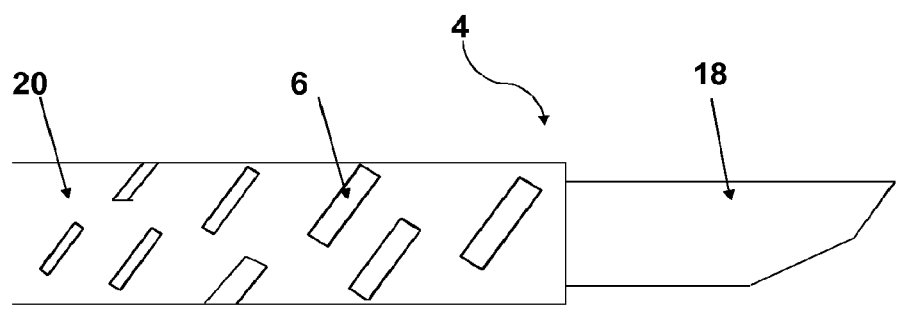
FIG. 5 represents a view of a delivery element comprising rectangular openings with a surface increasing in the distal direction.

FIG. 5 represents a schematic view of the distal tip 4 of the curved delivery element 2 according to an embodiment of the invention. The curved delivery element 2 is a sleeve 20 positioned above a piercing element 18. Said sleeve 20 comprises inclined rectangular openings 6 whose surface increases in the distal direction.

Figure 6:
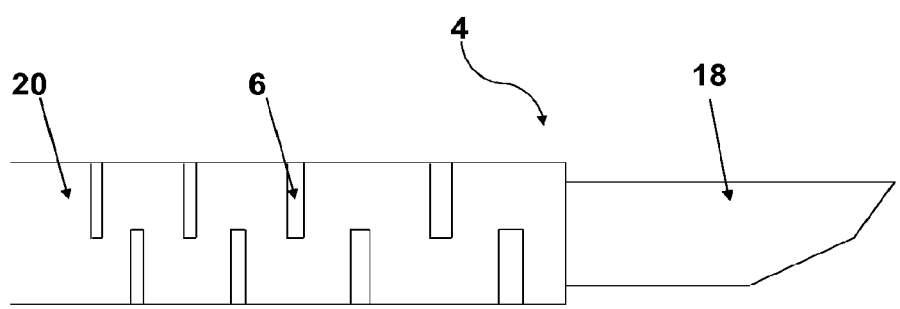
FIG. 6 represents a view of a delivery element comprising slit shaped openings.

FIG. 6 represents a schematic view of the distal tip 4 of the curved delivery element 2 according an embodiment of the invention. The curved delivery element 2 is a sleeve 20 positioned above a piercing element 18. Said sleeve 20 is comprised of slit-shaped openings 6.

Figure 7:
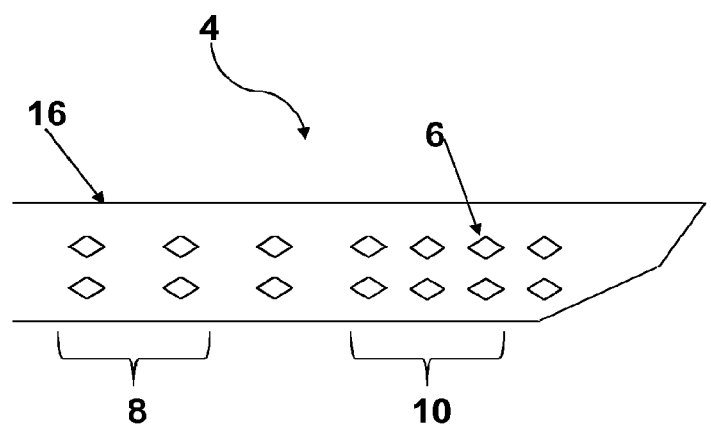
FIG. 7 represents a schematic view of a delivery element whose distal tip is comprised of two zones having different density of openings.

FIG. 7 represents a schematic view of the distal tip 4 of the curved delivery element 2 according to an embodiment of the invention. The curved delivery element 2 is a hollow needle 16 comprising openings 6 whose distal tip is comprised of two zones with a different density of openings. The density of the openings 6 increases in the distal direction. The specific surface of the openings 6 in the proximal zone 8 is smaller than the specific surface of the openings 6 in the distal zone 10.

Figure 10:
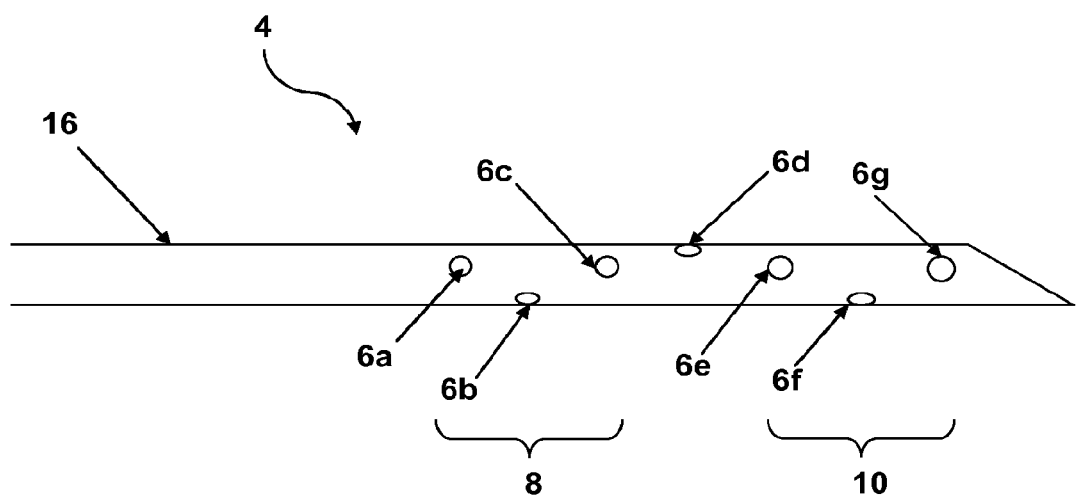
FIG. 10 represents a view of a delivery element comprising seven circular openings with a diameter increasing in the distal direction.

FIG. 10 represents a schematic view of the distal tip of a delivery element comprising seven circular openings with a diameter increasing in the distal direction. The openings 6a-g are disposed on the distal end 4 of the curved delivery element 2. Opening sizing (herein the diameter) increases in linear manner from opening 6a to 6g and is respectively 100 μm, 107 μm, 114 μm, 121 μm, 127 μm, 133 μm and 140 μm. The curvature of the delivery element is around 90°. The penetration depth is around 3.0 mm. The proximal zone 8 comprises holes 6a, 6b and 6c. The distal zone 10 comprises holes 6e, 6f and 6g. The length of the distal tip is about 4 mm. The length of the proximal and the distal zone is 1.133 mm each. The sum of the openings surface in the proximal zone is 0.027 mm$^2$. The specific surface in the proximal zone is 0.024 mm$^2$/mm. The sum of the openings surface in the distal zone is 0.0419 mm$^2$. The specific surface of the distal zone is 0.037 mm$^2$/mm.

Comparative Example 1

Figure 8:
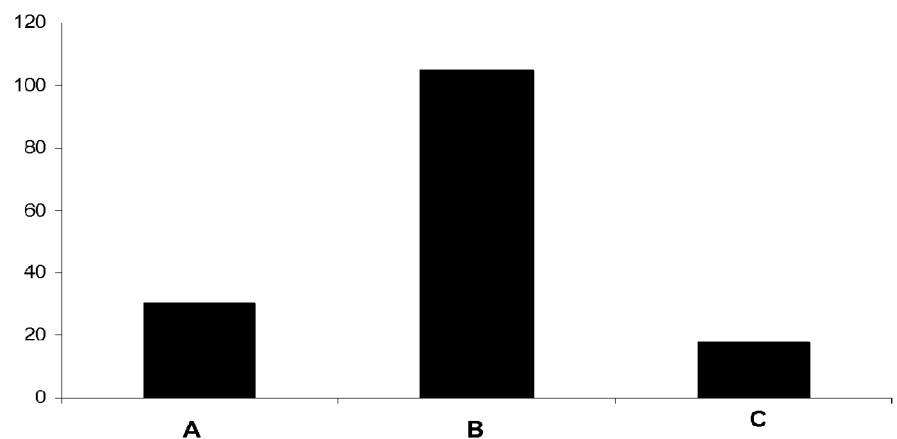
FIG. 8 represents a chart showing the retention capacity of a model solution of therapeutic agent in a substrate at an injection site. The microspheres were injected by various medical devices.

FIG. 8 represents a chart showing the retention of microspheres at the site where they are injected into the heart. The microspheres were injected through three different injection catheters. The first catheter A is the Myostar® delivery device comprised of, as a delivery element, a straight hollow needle comprised of only one opening in its distal tip. The second catheter B is an injection catheter, according to the invention. Catheter B comprises, as a delivery device, a hollow needle whose distal tip is comprised of five openings deployed radially. The openings, circular in shape, have a diameter increasing in the distal direction. The needle has a curved shape. The angle between the longitudinal axis running through the center of the lumen and the longitudinal axis running through the center of the distal opening is about 90°. In another embodiment, the angle may be around 100°. The third catheter C (Corkscrew) is comprised of, as a delivery element, a corkscrew-shaped, hollow needle. The needle is comprised of five circular openings on its distal tip, each having a diameter of 0.1 mm. FIG. 8 represents a chart displaying the capacity of retention of microspheres. The retention is expressed in the number of microspheres ($/10^3$) retained per gram of substrate, according to the injection catheter used. In this example, the substrate is a myocardium. The microspheres used are plastic balls 15 μm in diameter.

The tests were conducted on a pig myocardium ex-vivo. The heart is mounted on the PhysioHeart device (HemoLab, Eindhoven, Netherlands), which makes it possible to resuscitate the heart and keep it beating regularly (80 to 110 beats per minute) for several hours while perfusing oxygenated blood containing glucose. The distal tip of the injection catheter was positioned on the surface of the substrate, and then the delivery element of the injection catheter was slid inside the lumen and deployed inside the substrate. A solution of microspheres was injected. The microspheres were used as a model of a standard therapeutic agent. The solution of microspheres (2 ml containing 5 million microspheres) was injected for 1 minute at a constant speed.

Using catheter A, the rate of retention did not exceed 30.103 microspheres per gram of substrate, which is slightly greater than the retention obtained with the injection catheter C, with which a rate of retention of 18.103 microspheres per gram was attained. Thanks to the injection catheter B, according to the invention, the retention of microspheres per gram of substrate attained 105.103 microspheres per gram of substrate. The rate of retention is then approximately 30% in the isolated tissues. The retention of a therapeutic agent in the substrate is clearly improved thanks to the injection catheter, according to the invention.

Comparative Example 2

This comparative example aims to compare one commercially available catheter (Myostar supplied by Biologics Delivery System BDS—Johnson & Johnson) and two injection catheters according to the present invention. The study was based on the assessment of the fluorescent cells retention in myocardium of swine. All swine received one transepicardial injection into the anterior left ventricle wall after a left thoracotomy has exposed the heart. One injection of 50 million cells (provided by Transgenic Services, Charleroi, Belgium) in 0.5 ml was carried out in each swine left ventricle. The cells are GFP-labeled (GFP means Green Fluorescence Protein). The experimental procedure was carried out as follows:

T0—1 h30: premedication
T0—1 h15: physical evaluation and electrocardiogram
T0—1 h: anesthesia
T0—0.5 h: left thoracotomy
T0: one transepicardial injection in anterior left ventricle
T0+1 h: blood sampling and euthanasia After euthanasia, the heart was excised and tissue samples taken from the epicardial surface on the injection site (anterior mid-left ventricle wall) were analyzed. The analysis was carried out by counting, using fluorescence activated cell sorting (FACS), GFP-labelled cells retained in said tissue. It is also noted that during the procedure no arrhythmias was observed and that all swine survived.

Three catheters was compared and had the following configuration:

Catheter D was the Myostar with straight needle and no side holes.
Catheter E was a catheter according to the present invention. The Nitinol needle has 100° curved distal tip and is provided with 4 side holes.
Catheter F was a catheter according to the present invention. The Nitinol wire has 100° curved distal tip and a polyimide sheath containing 4 side holes disposed thereon.

Figure 9:
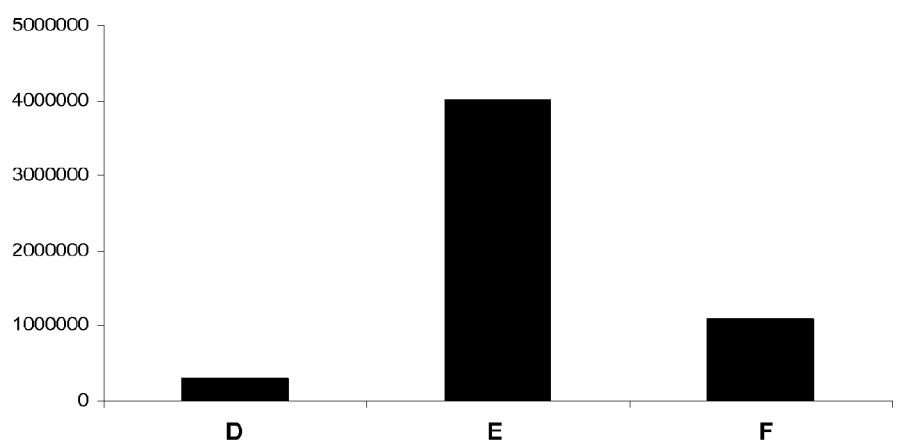
FIG. 9 represents a chart showing the retention of GFP-cells per gram at injection sites for three injection catheters.

The analysis of the tissues samples allowed the determination of the retention of cells at the injection site. The table 1 showed the average results from FACS analysis of tissues collected at injection site. FIG. 9 is a chart showing the number of GFP-cells per gram for the injection catheters tested.

TABLE 1

| Catheter | GFP-cells per 100000 cells | GFP-cells per gram |
| --- | --- | --- |
| D | 48.2 | 295790 |
| E | 653.2 | 4004388 |
| F | 175.8 | 1077691 |

These data clearly highlight that the injection catheters according to the present invention can surprisingly and dramatically enhance the retention of cells in the myocardium. This improvement is provided by the increasing in specific surface in distal direction as presently claimed.

The invention claimed is:

1. An injection catheter for delivering a therapeutic agent into a substrate, the injection catheter comprising:
   (i) a lumen that extends along the length of a longitudinal axis of the injection catheter and having an open distal end, the lumen being coaxial with the longitudinal axis of the injection catheter; and
   (ii) a curved delivery element,
   wherein the curved delivery element is deployed within the lumen when the curved delivery element is located outside of the substrate, the curved delivery element taking its curved shape distal to the open distal end of the lumen when deployed into the substrate through the open distal end of the lumen of the injection catheter, the curved delivery element including a hollow tube with a distal opening, the hollow tube having a proximal end and a distal end wherein the distal end comprises a distal tip portion, the distal tip portion of the hollow tube of the curved delivery element having at least two side openings wherein the at least two side openings are angularly displaced from each other about a longitudinal axis of the distal tip portion, the distal tip portion having a distal zone and a proximal zone, wherein a specific surface of the side openings in the distal zone is greater than a specific surface of the side openings in the proximal zone,
   wherein the specific surface of the side openings in the distal zone of the distal tip portion is the sum of a surface area of the side openings in the distal zone of the distal tip portion per unit of length of the distal zone measured along the longitudinal axis of the distal tip portion, and the specific surface of the side openings in the proximal zone is the sum of a surface area of the side openings in the proximal zone of the distal tip portion per unit of length of the proximal zone measured along the longitudinal axis of the distal tip portion,
   wherein the at least two side openings are suitable for delivering the therapeutic agent, where the therapeutic agent includes cells, and wherein the at least two side openings are configured to deliver the therapeutic agent with a flow rate that is less than 6 ml per minute.

2. The injection catheter of claim 1, wherein the specific surface of the side openings in the distal zone of the distal tip portion and the specific surface of the side openings in the proximal zone of the distal tip portion is between 0.01 mm$^2$/mm and 0.25 mm$^2$/mm.

3. The injection catheter of claim 1, wherein the specific surface of the side openings increases in a linear manner from a proximal end of the distal tip portion to a distal end of the distal tip portion.

4. The injection catheter of claim 1, wherein the side openings are arranged to allow for controlled distribution of the therapeutic agent.

5. The injection catheter of claim 1, wherein the distribution of the side openings in the distal tip portion is homogeneous.

6. The injection catheter of claim 1, wherein the specific surface of the side openings increases between the proximal zone and the distal zone by the increase in:
   (i) the mean surface of the side openings, or;
   (ii) the total surface of the side openings, or;
   (iii) the density of the number of side openings.

7. The injection catheter of claim 1, wherein a penetration depth of the curved delivery element in the substrate is controlled by the curvature of the curved delivery element, the curvature of the curved delivery element being defined by an angle between about 60 degrees and about 120 degrees between the longitudinal axis going through the center of the lumen when the injection catheter is positioned on the substrate in use and the longitudinal axis going through the center of the distal opening after deployment of the curved delivery element in the substrate.

8. The injection catheter of claim 7, wherein further control of the depth of penetration of the curved delivery element into the substrate is by way of an element detectable by ultrasound or other radiodetectable technique.

9. The injection catheter of claim 1, wherein the curved delivery element includes a hollow needle.

10. The injection catheter of claim 9, wherein an open surface area of the distal tip portion of the hollow needle is between 2 percent and 20 percent, wherein the open surface is the percentage of the total surface of the openings compared to the total surface of the distal tip of the delivery element.

11. The injection catheter of claim 1, wherein the curved delivery element comprises a sleeve positioned around a piercing element.

12. The injection catheter of claim 1, wherein the cells are human cells.

13. The injection catheter of claim 12, wherein the human cells are stem cells.

14. The injection catheter of claim 12, wherein the human cells are cardiac progenitor cells.

15. The injection catheter of claim 1, wherein the flow rate is less than 3 ml per minute.

16. The injection catheter of claim 1, further comprising a stop coupled to the curved delivery element to aid in determining a penetration depth of the curved delivery element when deployed in the substrate.

17. A method for delivering a therapeutic agent into a substrate using the injection catheter of claim 1, the method comprising:

positioning the open distal end of the lumen of the injection catheter on a surface of the substrate;

locating the curved delivery element of the injection catheter inside the lumen and deploying the curved delivery element into the substrate; and injecting the therapeutic agent into the substrate through the curved delivery element.

18. The method of claim 17, wherein a positive pressure is exerted on the proximal end of the injection catheter so as to deliver the therapeutic agent, and where the pressure is substantially constant for the duration of the delivery of the therapeutic agent.

19. The method of claim 17, further comprising controlling the penetration depth of the curved delivery element into the substrate.

20. The method of claim 19, wherein the penetration depth is between 25 percent and 75 percent of a thickness of the substrate.

21. The method of claim 17, wherein the therapeutic agent is delivered over a period of between about twenty seconds and about three minutes for a one mL quantity of the therapeutic agent.

22. The method of claim 17, wherein the substrate comprises the myocardium.

* * * * *